United States Patent
Kleinhout et al.

(10) Patent No.: US 10,214,616 B2
(45) Date of Patent: Feb. 26, 2019

(54) ANAEROBICALLY STORED BIOMASS HAVING HIGHLY REDUCED OR NO FERMENTATION

(71) Applicants: Arend Kleinhout, Store Heddinge (DK); Niels Juul Jensen, Harlev (DK); Kurt Falkenlove Madsen, Store Heddinge (DK)

(72) Inventors: Arend Kleinhout, Store Heddinge (DK); Niels Juul Jensen, Harlev (DK); Kurt Falkenlove Madsen, Store Heddinge (DK)

(*) Notice: Subject to any disclaimer, the term of this patent is extended or adjusted under 35 U.S.C. 154(b) by 19 days.

(21) Appl. No.: 15/302,651

(22) PCT Filed: Apr. 10, 2015

(86) PCT No.: PCT/EP2015/057855
§ 371 (c)(1),
(2) Date: Oct. 7, 2016

(87) PCT Pub. No.: WO2015/155336
PCT Pub. Date: Oct. 15, 2015

(65) Prior Publication Data
US 2017/0029572 A1 Feb. 2, 2017

(30) Foreign Application Priority Data

Apr. 11, 2014 (DK) .............................. 2014 00211

(51) Int. Cl.
| | | |
|---|---|---|
| C12P 7/00 | (2006.01) |
| C08H 8/00 | (2010.01) |
| C08H 7/00 | (2011.01) |
| C12P 7/10 | (2006.01) |
| A23K 40/00 | (2016.01) |
| A23K 10/30 | (2016.01) |
| A23K 50/10 | (2016.01) |
| A23K 50/30 | (2016.01) |
| A23K 30/15 | (2016.01) |

(52) U.S. Cl.
CPC .............. *C08H 8/00* (2013.01); *A23K 10/30* (2016.05); *A23K 30/15* (2016.05); *A23K 40/00* (2016.05); *A23K 50/10* (2016.05); *A23K 50/30* (2016.05); *C08H 6/00* (2013.01); *C12P 7/10* (2013.01); *Y02E 50/16* (2013.01)

(58) Field of Classification Search
None
See application file for complete search history.

(56) References Cited

U.S. PATENT DOCUMENTS

| | | |
|---|---|---|
| 9,139,851 B2 | 9/2015 | von Felde |
| 2008/0102502 A1 | 5/2008 | Foody et al. |
| 2009/0023187 A1 | 1/2009 | Foody et al. |
| 2016/0083808 A1* | 3/2016 | Ramarao ................ C12P 7/10 |
| | | 435/160 |
| 2017/0029572 A1* | 2/2017 | Kleinhout ............... C12P 7/10 |

FOREIGN PATENT DOCUMENTS

| | | |
|---|---|---|
| CN | 101205413 A | 6/2008 |
| WO | WO 02/37981 A2 | 5/2002 |
| WO | WO 2010/019935 A2 | 2/2010 |
| WO | WO 2010/126839 A2 | 11/2010 |

OTHER PUBLICATIONS

Kaliyan et al. (Biomass & Energy, vol. 33, 2009, pp. 337-359).*
Singh et al., "Acid and Alkaline Pretreatment of Lignocellulosic Biomass to Produce Ethanol as Biofuel," Int'l Journal of ChemTech Research, vol. 5, No. 2, Apr.-Jun. 2013, pp. 727-734.
Harmsen et al., "Literature Review of Physical and Chemical Pretreatment Processes for Lignocellulosic Biomass", ECN, 2010, pp. 1-49, see p. 23.
A. Kleinhout, "The Use of Fodder Beet as a Whole Crop: Experience in Denmark and Elsewhere", in Milk and Meat from Forage Crops, pp. 157-172 (1990).

* cited by examiner

*Primary Examiner* — Hope Robinson
(74) *Attorney, Agent, or Firm* — Fish & Richardson P.C.

(57) ABSTRACT

The present invention pertains among others to a method of preparing a biomass mash from a biomass comprising lignin. The invention also pertains to a biomass mash comprising reduced viscosity.

29 Claims, 1 Drawing Sheet

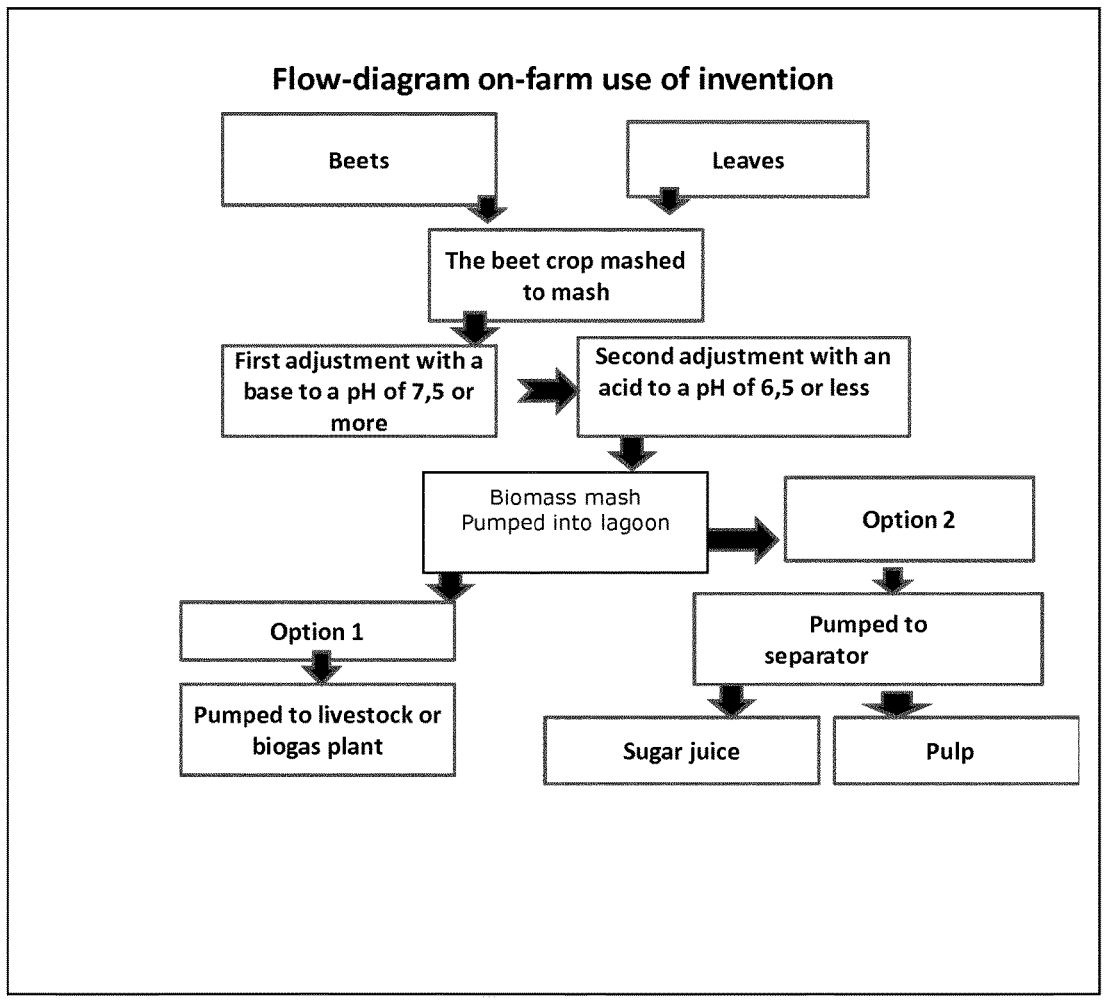

ANAEROBICALLY STORED BIOMASS HAVING HIGHLY REDUCED OR NO FERMENTATION

CROSS-REFERENCE TO RELATED APPLICATIONS

This application is a U.S. national stage application under 35 U.S.C. § 371 of International Application No. PCT/EP2015/057855, filed on Apr. 10, 2015, which claims priority to Danish Patent Application No. PA 2014 00211, filed on Apr. 11, 2014, the entire contents of each of which are incorporated herein by reference.

TECHNICAL FIELD OF THE INVENTION

The present invention relates to a method of preparing a biomass to a biomass mash. In particular, the present invention relates to a method of preparing a biomass mash through a combination of pH adjustment steps at a temperature from 1 to 40° C.

BACKGROUND OF THE INVENTION

The adaptation of biomass mash to long-term storage, handling and use as a feedstock in animal feeding as well as substrate for the production of semi-manufactured products, such as sugar juice has been hampered by high viscosity of the biomass mash and low control on the fermentation process under anaerobic conditions. These two factors combined have posed a major impediment on the perspectives of biomass mash as a source of a homogeneous feed and of semi-manufactured products.

Combined base-acid treatments referred to in the literature, such as US 2008 102502, relate to an energy-intensive destruction of ligno-cellulosic biomass in biomass comprising a high lignin content at highly elevated temperatures, often in combination with enzymes.

Hence, a less energy consuming method of preparing a high feed quality biomass mash would be advantageous. Moreover it would be advantageous to provide a biomass mash having reduced viscosity.

SUMMARY OF THE INVENTION

Thus, an object of the present invention relates to a method of preparing a biomass mash.

In particular, it may be seen as an object of the present invention to provide a method and biomass product that solves the above mentioned problems of the prior art.

Thus, one aspect of the invention relates to a method of preparing a biomass mash wherein a biomass comprising lignin in an amount of less than 10% and/or a Neutral Detergent Fibre (NDF) value of less than 65% of the dry matter content is subjected to a first pH adjusting step, in which the pH is adjusted with a base to a pH of at least 7.5 at a temperature of 1-40° C. in a period of at least 5 minutes, followed by a second pH adjusting step, wherein the pH of the biomass mash is adjusted with an acid to a pH in the range of 1 to 6.5, thereby obtaining a biomass mash.

Another aspect of the present invention pertains to a biomass mash comprising a viscosity in the range from 2-5 Centipose.

A further aspect of the present invention pertains to the use of said biomass mash for the production of feed, bio-fuel and other industrial products.

BRIEF DESCRIPTION OF THE FIGURES

FIG. 1 shows a flow chart in one of many scenarios of an on-farm produced biomass mash and the subsequent steps of further use. Thus, the flow-diagram illustrates one practical scenario out of many possibilities.

With the beet crop as source of biomass, the beets and leaves are harvested separately. The beets are cleaned, destoned and mashed and subsequently mixed with mashed leaves. Subsequently, this biomass mash is subjected to the first pH adjusting step, followed by the second pH adjusting step and thereupon pumped into a lagoon, where it can be stored from anywhere in between a few days to a year or more.

Thereupon, on a daily basis or at other time intervals, the biomass mash in the lagoon can be pumped to livestock, biogas plants or alternatively to a separation unit which separates the biomass mash into sugar juice and pulp. The pulp can be stored anaerobically in a stack whereas the sugar juice will be stored in a tank or air-tight tower silo.

The flow-diagram illustrates the two process-lines which can be pursued. Some users will solely improve the viscosity of their biomass mass by no-fermentation and pump this feedstock to their livestock or biogas digesters, as illustrated in option 1.

Other users want to extend the use of their biomass mash by separating sugar juice from the mash. Whereas the sugar juice is sold on the market of fermentable sugars, the remaining pulp is fed to livestock, biogas digesters or sold as a substrate for the production of protein pellets, such as illustrated in option 2.

Another scenario could be based on a batch system in which the chemical treatment is applied on a daily basis or at regular time intervals. In this scenario, fresh beets, stored in clamps, can be the daily source, with an anaerobic storage limited to sugar juice.

The present invention will now be described in more detail in the following.

DETAILED DESCRIPTION OF THE INVENTION

In a first aspect the present invention pertains to a method of preparing a biomass mash, wherein a biomass comprising lignin in an amount of less than 10% and/or a Neutral Detergent Fibre (NDF) value of less than 65% of the dry matter content is subjected to a first pH adjusting step, in which the pH is adjusted with a base to a pH of at least 7.5 at a temperature of 1-40° C. in a period of at least 5 minutes, followed by a second pH adjusting step, wherein the pH of the biomass mass is adjusted with an acid to a pH in the range of 1-6.5, thereby obtaining a biomass mash.

The method may further comprise a step of separating the biomass mash into (i) a liquid fraction and (ii) a non-liquid fraction following the second pH adjustment step. Such a separation may be performed using a Vincent press, screw press, drum sieve or centrifuge.

The liquid fraction may be a juice whereas the non-liquid faction may be a pulp.

The biomass may be selected from the group consisting of alfalfa, green alfalfa, corn, grass, clover, beets, peas, beans, whole crop cereals, sweet sorghum, sorghum, sun flowers and mixtures thereof.

The grasses may be cool season or tropical grasses and the clover may be white, red, alsike or other clovers.

In an embodiment of the present invention the biomass may comprise lignin in an amount of less than 10% of the dry matter content, such as less than 9%, e.g. less than 8%, such as less than 7%, e.g. less than 6%, such as less than 5%, e.g. less than 4%, such as less than 3%, e.g. less than 2.5%, such as less than 2% e.g. less than 1.5%, such as less than 1% of the dry matter content, e.g. in the range from 1-9% of the dry matter content, e.g. in the range from 2-8%, such as in the range form 3-7%, e.g. in the range from 4-6%, such as in the range from 5-8% of the dry matter content. In a preferred embodiment the biomass comprise lignin in an amount of less than 3.5% of the dry matter content and preferably around 3% of the dry matter content.

Applying a biomass low in lignin is preferred since lignin cannot be used by animals (independent of whether these animals are ruminant or non-ruminant). Thus a biomass or a biomass mash low in lignin comprise a higher feed value compared to a biomass or biomass mash high in lignin as illustrated in table 8.

In an embodiment of the present invention the biomass may comprise a Neutral Detergent Fibre (NDF) value of less than 65% of the dry matter content, such as less than 60%, e.g. less than 55%, such as less than 50%, e.g. less than 45%, such as less than 40%, e.g. less than 35%, such as less than 30%, e.g. less than 25%, such as less than 20% of the dry matter content, such as less than 15%, e.g. less than 10%, such as less than 5% of the dry matter content, e.g. in the range from 5-65% of the dry matter content, e.g. in the range from 10-60%, such as in the range form 15-55%, e.g. in the range from 20-50%, such as in the range from 25-45% of the dry matter content, e.g. in the range from 30-40%, such as in the range from 35-40% of the dry matter content.

In an embodiment of the present invention the pH in the first pH adjustment step may be adjusted with a base to 7.5 or more, such as 8 or more, e.g. 9 or more, such as 10 or more, such as 11 or more, e.g. 12 or more, such as 13 or more, e.g. 14, such as in the range from 7.5-14, e.g. in the range from 8-13, such as in the range from 9-12, e.g. in the range from 10-11, such as in the range from 10-14.

In a preferred embodiment of the present invention the pH in the first pH adjustment step may be adjusted with a base to 10 or more.

In an embodiment of the present invention pH is adjusted with a base in the first pH adjusting step in a period of at least 5 minutes, such as at least 10 minutes, e.g. at least 20 minutes, such as at least 30 minutes, e.g. at least 40 minutes, such as at least 50 minutes, e.g. at least 60 minutes, such as at least 1 hour e.g. at least 2 hours, such as at least 1 hour e.g. at least 2 hours, such as at least 3 hour e.g. at least 4 hours, such as at least 5 hour e.g. at least 6 hours, such as at least 7 hour e.g. at least 8 hours, such as at least 9 hour e.g. at least 10 hours, such as at least 11 hour e.g. at least 12 hours, such as at least 13 hour e.g. at least 14 hours, such as at least 15 hour e.g. at least 16 hours, such as at least 17 hour e.g. at least 18 hours, such as at least 19 hour e.g. at least 20 hours, such as at least 21 hour e.g. at least 22 hours, such as at least 23 hour e.g. at least 24 hours, such as at least 1 day, e.g. at least 2 days. The first pH adjustment step may in principle last for several days to a year or several years.

In a further embodiment of the present invention the pH in the second pH adjustment step may be adjusted with an acid to a pH in the range from 1-6.5, e.g. in the range from 2-5, such as in the range from 3-4.

In a preferred embodiment of the present invention the pH in the second pH adjustment step may be adjusted with an acid to a pH in the range from 3-6.

This combination of pH adjusting steps provides a biomass mass having no microbial activity and therefore improved stability when stored under anaerobic conditions and an improved window in time to sustain a high quality feed stock under aerobic conditions. Thus, by applying the method of the present invention it is possible to reduce storage losses due to the improved anaerobic stability and feeding losses due to aerobic stability. On farm this may be useful since the biomass may be stored from one growth season to another, as well as providing a significantly lengthened window of time in feeding the biomass without dry matter losses when exposed to aerobic conditions.

In an embodiment of the present invention the temperature during the entire process may be from 1-40° C., such as in the range from 2-39° C., e.g. from 3-38° C., such as in the range from 4-37° C., e.g. from 3-38° C., such as in the range from 4-37° C., e.g. from 5-36° C., such as in the range from 6-35° C., e.g. from 7-34° C., such as in the range from 8-33° C., e.g. from 9-32° C., such as in the range from 10-31° C., e.g. from 11-30° C., such as in the range from 12-29° C., e.g. from 13-28° C., such as in the range from 14-27° C., e.g. from 15-26° C., such as in the range from 16-25° C., e.g. from 17-24° C., such as in the range from 18-23° C., e.g. from 19-24° C., such as in the range from 20-23° C., e.g. from 21-22° C., such as below 40° C., e.g. below 39° C., such as below 38° C., e.g. below 37° C., such as below 36° C., e.g. below 35° C., such as below 34° C., e.g. below 33° C., such as below 32° C., e.g. below 31° C., such as below 30° C., e.g. below 29° C., such as below 28° C., e.g. below 27° C., such as below 26° C., e.g. below 25° C., such as below 24° C., e.g. below 23° C., such as below 22° C., e.g. below 21° C., such as below 20° C., e.g. below 19° C., such as below 18° C., e.g. below 17° C., such as below 16° C., e.g. below 15° C., such as below 14° C., e.g. below 13° C., such as below 12° C., e.g. below 11° C., such as below 10° C., e.g. below 9° C., such as below 8° C., e.g. below 7° C., such as below 6° C., e.g. below 5° C., such as below 4° C., e.g. below 3° C., such as below 2° C., e.g. below 1° C.

In a preferred embodiment of the present invention the temperature during the entire process may be from 5-25° C.

The inventors of the present invention discovered that by applying the two pH adjusting steps in combination with low temperatures (compared to the prior art which uses temperatures over 100° C.) it was possibly to obtain a biomass mash simultaneously having low viscosity, improved draining properties and improved homogenization. The low viscosity is due to the break down of pectin and thus, decreased amount of pectin in the biomass mash of the present invention (less liquid is simply adsorbed by the pectin in the biomass mash of the present invention compared to traditional biomass mash products). The improved drainage is also due to the decreased amount of pectin in the biomass mash of the present invention—following option 2 in FIG. 1 less liquid is bound by pectin in the biomass mash, thus by applying the method of the present invention it is possible to increase the amount of sugar juice obtained at lesser energy-input when separating the biomass mash into sugar juice and pulp. The improved homogenization is also due to the decreased amount of pectin thus, it the force which is used to homogenize the biomass mass before use is decreased compared to the force which have to be used when homogenizing a biomass mash having higher viscosity.

The biomass may be pretreated by mechanical processes such as but not limited to grinding, milling, hacking, squeezing, slicing, abrading, pressing, crushing, chipping, refining and combination thereof.

In one embodiment of the present invention the base may be selected from the group consisting of sodium hydroxide (NaOH), potassium hydroxide (KOH), ammonium hydroxide ($NH_4OH$), calcium hydroxide ($Ca(OH)_2$) and mixtures thereof.

In a preferred embodiment the base may be selected from the group consisting of sodium hydroxide (NaOH), potassium hydroxide (KOH) and mixtures thereof.

In a further embodiment the acid may be selected from the group consisting of nitric acid ($HNO_3$), phosphoric acid ($H_3PO_4$), hydrochloric acid (HCL), urea ($CO(NH_2)_2$) and mixtures thereof.

In a preferred embodiment the base may be selected from the group consisting of nitric acid ($HNO_3$), urea ($CO(NH_2)_2$) and mixtures thereof.

Adding sulfuric acid as an acid in the second pH adjusting step should preferably be avoided since sulphuric acid will change the taste of the biomass mash obtained—thus, if such a biomass mash is feed to livestock animals, the taste will lead to a reduced feed intake.

In one embodiment the present invention pertains to a biomass mash comprising a viscosity in the range of 2-5 Centipose, e.g. in the range from 3-4 Centipose, such as below 5 Centipose, e.g. below 4 Centipose, such as below 3 Centipose, e.g. below 2 Centipose, such as below 1 Centipose.

In an embodiment of the present invention the biomass comprises a viscosity in the range of 15-30 Centipose, e.g. in the range from 16-29 Centipose, such as in the range from 17-28 Centipose, e.g. in the range from 18-27 Centipose, such as in the range from 19-26 Centipose, e.g. in the range from 20-25 Centipose, such as in the range from 21-24 Centipose, e.g. in the range from 22-23 Centipose.

Viscosity may be measured according to the method disclosed in Eko Hidayanto et al, 2010 (3).

In an embodiment of the present invention the biomass comprises pectin in an amount of 2-3% of the dry matter content.

In a further embodiment of the present invention the biomass mash comprises pectin in an amount of less than 0.25% of the dry matter content, such as less than 0.2%, e.g. less than 0.15%, such as less than 0.1%, e.g. less than 0.05% of the dry matter content. As mentioned previously, it is preferred to have pectin in low amounts in the biomass mash due to the effect of pectin of the viscocity—thus, it may be preferred that the biomass mash comprise pectin in amount of 0% of the dry matter content.

The amount of pectin may be measured according to the method disclosed in S. Okimasu, 2014 (4).

In a preferred embodiment the present invention pertains to a biomass mash simultaneously comprising a viscosity in the range of 2-5 Centipose and pectin in an amount of less than 0.25% of the dry matter content.

In a further embodiment the biomass mash may comprise at the most 3.5% lignin of the dry matter content, such as at the most 3%, e.g. at the most 2.5%, such as at the most 2%, e.g. at the most 1.5%, such as at the most 1% of the dry matter content, e.g. in the range from 0-3.5% lignin of the dry matter content, e.g. in the range from 0.5-3%, such as in the range from 1-2.5, e.g. in the range from 1.5-2% lignin of the dry matter content.

In a preferred embodiment the biomass mash may comprise at the most 2% lignin of the dry matter content.

In another embodiment of the present invention the biomass mash may comprise a log CFU of 0/gram biomass mash.

In a further aspect the present invention pertains to the use of the biomass mash for the production of feed, bio-fuel and other industrial products.

Thus, in one embodiment of the present invention the liquid fraction may be used for the production of feed, bio-fuel and other industrial products. In another embodiment the non-liquid fraction may be used for the production of feed. The feed may be animal feed.

In the present context the terms biomass mash may be termed silage or biomass silage if stored under anaerobic conditions.

In the present context the term biomass mash and the term mash are used herein interchangeably.

The biomass mash obtained by the present invention has improved viscosity, drainage and homogenization potential, a pH-value of choice and reduced storage losses by improved aerobic stability in order to optimize process-lines in bio-energy, animal feed and industrial production of bioproducts.

This invention deals with two major issues. For one, an improved on-farm homogenization, long-term storage and handling of biomass per se, as an animal feed or feedstock in a biogas plant as such.

Secondly, providing the opportunity, either on-farm, at a factory or through a combination of both, to split the biomass into a liquid (such as but not limited to a juice) and a non-liquid fraction (such as but not limited to a pulp). Such separation may be performed following the second pH adjustment step.

Whereas the liquid fraction will serve as the substrate of a semi-manufactured product (e.g. sugar juice) for industrial purposes, the remaining non-liquid fraction is a valued animal feed respectively a source for protein or energy production.

The side-effects of this non-enzymatic method have a favorable effect on a multifold of important parameters of the biomass per se, that is on both the liquid- and non-liquid fraction. With no fermentation to take place, sugar levels are sustained, dry matter losses are reduced by improved anaerobic and aerobic stability in both fractions. Moreover it improves the process economy that neither enzymes nor heat need to be added to the method of the present invention nor to the obtained biomass mash.

Definitions of Biomass:

Biomass is biological material derived from living, or recently living organisms. It most often refers to plants or plant-derived materials which are specifically called lignin-cellulosic biomass. As an energy source, biomass can either be used directly via combustion to produce heat and electricity, or indirectly after converting it to various forms of bio-energy including bio-fuel.

The concept of biomass in this application relates to plant-derived materials and covers, defines and reflects the same understanding and reach as the one defined above, however, with specific focus on the feeding of farm animals, production of amino-acids and proteins and/or semi-manufactured products, such as sugar juice, for the production of ethanol, other energy sources or high-value industrial products, among which, crystal Sugar, Plastic, Enzymes, Antibiotics, etc.

The quality of biomass as a feedstock for most purposes is expressed as a percentage of lignin and/or of the Neutral Detergent Fiber (in short NDF) of the Dry Matter. Lignin is the indigestible fiber with no energy value to the animal. NDF is a measurement of the total fiber content of a feedstock/forage, composed of cellulose, hemicelluloses, lignin and the remaining ash content.

As illustrated in table 1 and within the context of quality, biomass within this application is defined for the organic materials referred to above with a lignin content of less than 10% and a NDF value of less than 65% of the Dry Matter as measured by the analysis of P. J. van Soest (1).

Within biomass the following distinctions will be pursued in this invention. We distinguish wet biomass (in short "mash") i.e. biomass mash which can be drained into a liquid fraction (in short "sugar juice") and a non-liquid fraction (in short "pulp").

Bioproducts or biobased products, referred to in this application, may be materials, chemicals and energy derived from Renewable Biological Resources.

The beet crop may be a choice of biomass:

This invention finds its origin in work on the beet crop (*Beta vulgaris*). Beet is the main producer of sugar in the northern part of the hemisphere and adapted to a wide range of climatic conditions. In terms of energy production per hectare, a crop of beet out-yields any crop within this climatic range, in particular if the beet tops are included in the equation.

On top of that, as table 6 clearly indicates, beet may be a favorable choice of biomass when it comes to the production of sucrose as well as alternatively, to the quantity of glucose and fructose per ha upon hydrolysis of sucrose. As can be seen in table 7 the pH of the biomass mash obtained by the present invention influences the sugar species present in the biomass mash after the second pH adjustment.

In the general understanding hitherto, beets are either used for the industrial production of sugar or as a feedstock in animals and biogas plants. Throughout history this distinction has led to the development of high dry matter sugar beet varieties on the one side and varieties of feed beet of lower dry matter content on the other side.

As to this invention, the entire range of varieties, from sugar- to low dry matter feed beets (in short "beets") within the species *Beta vulgaris* may be applied as a suitable biomass, including the tops (in short "beet crop" which covers both the beet including the beet top). Thus, in an embodiment of the present invention the biomass may be beet and/or beet top preferably of the species *Beta vulgaris*.

The validity of the observations on the beet crop and the respective claims on that account, however, do apply for other biomass sources, as defined above.

Short and long-term storage of biomass, state of the art of as to-day:

Long-term storage of biomass in general is hitherto realized through hay or silage. Silage is the result of anaerobic storage, whereby sugars, in part or total, as demonstrated in table 3 are fermented into organic acids, which, in turn, are the vehicles in preserving biomass. Silage additives are on the market to optimize the fermentation process by unfavorable harvest conditions as illustrated in table 5.

Nowadays, most farmers are well-acquainted with making silage, with a reduction of the fermentation losses as low as 8-10% of the dry matter in "good silage" as the immediate consequence.

In the beet crop two separate products viz. beet and tops are recognized. Throughout the past centuries the focus has been on the energy-rich beets, whereas the use of tops progressively lost terrain during the last 50 years.

Traditional storage and handling of fresh beets:

Traditionally beets were stored in clamps. Storage in clamps, however, has often been hampered by significant dry matter losses, either due to temperatures below freezing point or higher than 10° C. Particularly on account of the high losses with increased temperature, this practice was limited to the winter period and early spring.

Particularly in the northern part of Europe, the work involved in the prevention of significant dry matter losses in clamps as well as in the subsequent feeding of the beets led to a heavy daily workload of high costs. This in turn did not harmonize with the progressive increase in scale of farm operations of the last 50 years, reducing beet as a fodder crop from a one-time high (e.g. 120.000 ha in DK in 1960) to a record low acreage all across Europe (e.g. 3.000 ha in DK in 2010).

Whereas the ensiling of beet tops together with chopped straw was practiced to a limited extent, in most cases this valuable protein feed was left on the field and ploughed under, leading to a reduced need for fertilizers in a successive crop but also to an increased leaching of $NO_3$ in the fall.

Recent developments in the storage and handling of beets:

In recent developments the beets are mashed and pumped into a lagoon for daily use by short or long term storage, from 1 day to a year or more, under anaerobic conditions, also as silage. This approach has solved many of the problems associated with the traditional storage and handling, referred to above, and led to a renewed interest in beet in Germany and Denmark.

Important to note is, even storage of biomass as a mash or liquid of short duration, leads, in part or total, to anaerobic conditions.

The remaining problems in the storage and handling of beets:

Whereas these recent developments address the problem of storage and handling to a large extent, the high viscosity, table 2 and the fermentation of sugars into variable degrees of pH, organic acids, etc, such as illustrated in table 3, are not solved. In fact, compared to fresh beets, cattle feed with the feeds of the prior art (i.e. ensilage which lack sugar or sugar species due to fermentation under anaerobic conditions) also have to be fed protein supplements as a compensation for the lack of sugar present in the feed. In contrast the biomass mash of the present invention comprise sugar or sugar species (i.e. sucrose, glucose and/or fructose) since these sugars are not degraded when the biomass mash is stored under anaerobic conditions.

Viscosity of the biomass mash is a major factor in the efficiency of handling biomass mash:

Although beet respectively the beet crop has a dry matter percentage of only 15 to 25%, dependent on the variety, the mash thereof is a "thick" fluid, difficult and energy demanding to stir and homogenize to a feedstock of similar composition from day to day. To sustain a high daily production of milk, the latter is of significant importance in the feeding of high performing cows, highly dependent, as they are, on a consistent ration from day to day.

If it comes to the separation of sugar juice from mash a great difficulty in doing so is observed by present-day equipment, such as the Vincent press, the different sieve-based systems, etc. The water retention capacity of biomass is an apparent significant draw-back in maximizing the liquid fraction.

Whether as a feed stock in biogas, in the production of milk and meat or in separating the mash into sugar juice and pulp, coming to grips with this "thickness" of the mash will have far reaching effects on the economic perspectives in using beet, or other biomass for that matter. In professional terms, "thickness" of the liquid state is expressed in viscosity, as referred to in table 2.

An enzyme containing commercial product BC-Zym leads to lower viscosities and a better fluidity of biomass. Silage additives including enzymes, are often extensive, sensitive to temperature and pH, whereas their effective use is hard to visualize in lagoons of 10.000 m3 or more. The major drawback, however, is the fact that enzymatic treatments do not stop the fermentation process with uncontrolled pH-values and the undesired breakdown of sugar as a result.

However, the goal and characteristic of this invention is the combination of a reduced viscosity and improved drainage potential by also sustaining the desired sugar levels under storage conditions of whatever duration Pectin poses the viscosity problem in present-day technology:

The major obstacle in lowering the viscosity of the biomass is pectin. Pectin is a structural heteropolysaccharide contained in the primary cell-walls of plants and fruits and can bind water up to 15 times its own weight.

In a conscious effort, at normal temperatures, to destroy pectin by raising pH-levels from 7.5 to 14 by a non-enzymatic alkaline treatment, in a series of experiments on mash of beet respectively of the beet crop, a drastic reduction of the viscosity by up to 70% on the Cp scale was observed as illustrated in table 2.

Simultaneously a significant improvement on the ease of the homogenization of the mash respectively on the separation of the fluid from the mash could be observed. This in turn led to a larger liquid fraction by a lower energy-use.

Alternatively both enzymes and high temperatures above 80 degrees C. destroy pectin, but at the cost of extra financial costs. Enzymes are expensive whereas high temperatures are costly in energy.

Microorganism pose the fermentation problem in present-day technology:

The alkaline treatment referred to in this invention has another effect of major importance. At pH levels of 7.5 or more, microorganism and presumably their spores are killed and in contrast to silage additives, such as illustrated in table 5, not as a function of the fermentation process.

Bacteria and yeasts are major vehicles in the fermentation process under anaerobic conditions as well as in the respiration and rotting process when exposed to air. Hence, the overall death of microorganisms, including fungi implies both a significantly reduced fermentation of sugars by improved aerobic stability of the silage upon exposing the mash to air, as illustrated in table 5.

Exposing anaerobe stored biomass to air leads to heat development and progressively increasing losses. Aerobic stability, in this context, refers to the number of days in between the onset of exposing the biomass to air and the first development of heat at a predefined temperature and is highly correlated with bacterial and fungal death.

In terms of handling biomass, aerobic stability provides flexibility and a larger window of time to operate within an aerobic environment without losses. Biomass, particularly of the beet crop, often includes soil and microbial contamination. The bactericidal respectively fungicidal effect of the alkaline treatment, allows a window for contaminated biomass in the efforts pursued.

Thus, the method provides a viscosity of the biomass mash which is strongly reduced by merely applying normal daily temperatures—this on the other hand implies a local and cost-effective long-term storage system of biomass mash at low dry matter losses and chosen pH.

The acid treatment regulates and controls the pH of the mash:

one aspect of the present invention is the quality of sugar juice, that is, on the disaccharide sucrose and the monosaccharides glucose and fructose, such as illustrated in table 6.

An aggressive alkaline treatment under high temperatures easily destroys the monosaccharides, whereas sustaining a pH of the sugar juice, lower than 5, will revert sucrose into glucose and fructose. Depending on the process-line to be pursued on the sugar juice, different sugar qualities/species/varieties are on demand, each of them sustained at their optimum pH.

In terms of sustaining sucrose, pH levels of 5 to 6.5—whereas in ethanol production pH levels of 4.5 to 5.5 of the sugar juice are to be pursued. In animal feeding, pH's of 3-5 of the pulp are on demand.

To preserve this delicate balance of sucrose, fructose and glucose, the alkaline treatment of the biomass is limited from 0.15 hours—some days and followed by an acid treatment to reduce the pH to the optimum levels specified above. If the sugar juice can be of lesser quality, the alkaline treatment can be prolonged to an unlimited number of days, all of them routes this invention has made possible.

Thus, in one embodiment of the present invention the invention pertains to a method which substantially sustains disaccharides in the biomass and/or biomass mash and prevents their breakdown into glucose and fructose In one embodiment of the present invention the invention pertains to a method which delivers 93-95% sucrose and 0.6-5.8% glucose as % of total sugars of the sugar species in the biomass mash and/or the liquid fraction obtainable from said biomass mash, as illustrated in table 6.

In a further embodiment the invention pertains to a method of preparing a biomass mash, said biomass mash comprising 93-95% sucrose and 0.6-5.8% glucose as % of total sugars of the sugar species in the biomass mash and/or the liquid fraction obtainable from said biomass mash. Thus, in another embodiment the present invention pertains to biomass mash and/or the liquid fraction obtainable from said biomass mash comprising 93-95% sucrose and 0.6-5.8% glucose as % of total sugars of the sugar species in the biomass mash and/or the liquid fraction obtainable from said biomass mash.

Thus, in one embodiment of the present invention the invention pertains to a method which delivers 47-50% glucose and 52-53% fructose as % of total sugars of the sugar species in the biomass mash and/or the liquid fraction obtainable from said biomass mash, such as illustrated in table 6.

In a further embodiment the invention pertains to a method of preparing a biomass mash, said biomass mash comprising 47-50% glucose and 52-53% fructose as % of total sugars of the sugar species in the biomass mash and/or the liquid fraction obtainable from said biomass mash. Thus, in another embodiment the present invention pertains to biomass mash and/or the liquid fraction obtainable from said biomass mash comprising 47-50% glucose and 52-53% fructose as % of total sugars of the sugar species in the biomass mash and/or the liquid fraction obtainable from said biomass mash.

Thus, in one embodiment of the present invention the invention pertains to a method which is based on free fermentable sugars rather than the fixed fermentable sugars in biomass.

In a further embodiment the invention pertains to a method of preparing a biomass mash, wherein the majority of sugar species are free fermentable sugars.

Thus, in one embodiment of the present invention the invention pertains to a method which is based on free fermentable sugars and is therefore far more cost-effective than the pursuit of fixed fermentable sugars in biomass.

Thus, in one embodiment of the present invention the invention pertains to a method which delivers a sterilized product (i.e. the biomass mash and/or the liquid fraction obtainable from said biomass mash and/or the non-liquid fraction obtainable from said biomass mash), thus saving process-costs down the process-line.

In one embodiment the biomass mash obtainable by the method of the present invention and or the biomass mash of the present invention may be sterile.

Thus, in one embodiment of the present invention the invention pertains to a method, which delivers 93-95% sucrose and 0.6-5.8% glucose of total sugars as the sugar species.

In a further embodiment the invention pertains to a method of preparing a biomass mash, said biomass mash comprising 93-95% sucrose and 0.6-5.8% glucose of total sugars as the sugar species in the biomass mash and/or the liquid fraction obtainable from said biomass mash. Thus, in another embodiment the present invention pertains to biomass mash and/or the liquid fraction obtainable from said biomass mash comprising 93-95% sucrose and 0.6-5.8% glucose of total sugars as the sugar species in the biomass mash and/or the liquid fraction obtainable from said biomass mash.

Thus, in one embodiment of the present invention the invention pertains to a method which delivers 47-50% glucose and 52-53% fructose of total sugars as the sugar species.

In a further embodiment the invention pertains to a method of preparing a biomass mash, said biomass mash comprising 47-50% glucose and 52-53% fructose of total sugars as the sugar species in the biomass mash and/or the liquid fraction obtainable from said biomass mash. Thus, in another embodiment the present invention pertains to biomass mash and/or the liquid fraction obtainable from said biomass mash comprising 47-50% glucose and 52-53% fructose of total sugars as the sugar species in the biomass mash and/or the liquid fraction obtainable from said biomass mash.

Alkaline treatments are known to lead to a better digestibility of feed:

Years of experience in the treatment of straw with the strong bases NaOH respectively $NH_4OH$, indicate a significant improvement in the digestibility of that straw in cattle at even moderate pH-levels. This supports the view of a breakdown of the ligno-cellulosic complex in biomass at moderate pH levels in between 6-7, let alone at pH levels in the top end of 10-14.

Polysaccharides are long chains of linked glucose units in the case of cellulose, of linked different units of monosaccharides in hemi-cellulose and of galacturonic acid in the case of pectin. Their break-down leads in part or total to the production of additional C6 and C5 sugars, improving digestibility and sugar yields.

Hence, through the partial break-down of this ligno-cellulosic complex, the digestibility or improved speed of digestion of the feed fraction, which is an important criteria in feed quality as well as the amount of readily available sugars will be increased.

An aspect of the present invention pertains to sustaining sugar quality, limiting the duration of exposure to a high pH from a few minutes to a few days at daily temperatures. Hence, a break-down of the ligno-cellulosic complex under those conditions has not been documented as yet.

However, as to the other target of this invention, that is, operations solely focused on a feedstock for biogas plants and livestock, a prolonged period at high pH followed by a prolonged period at low pH of the biomass mash, likely will lead to a partial breakdown of the ligno-cellulosic complex and improved digestibility.

The invention compared to methods to destroy the ligno-cellulosic complex:

To reduce the competition on acreage for energy rather than for food/feed, the focus in the production of bio-energy is on the hydrolysis of the lignin-cellulosic complex of so-called $2^{nd}$ generation biomass (straw, wild growing grasses, etc.), In particular in the production of ethanol on $2^{nd}$ generation biomass, harsh methods are applied which are based on steam, often in combination with enzymes, strong bases and/or strong acids at elevated moisture and temperature.

In contrast to this invention, these treatments are energy-demanding and not adapted to sustain sugar quality and a pH upon choice, as elaborated above.

The non-enzymatic method proposed of this invention functions at normal daily temperature averages, above 5° C., anywhere in the world at any time of the year. The invention is based on a low-input technology in the production of sugar juice and pulp.

Other base and acid treatments to realize the invention:

As to the alkaline treatment, alternative to the bases NaOH, KOH or mixtures thereof, $NH_4OH$ and/or $Ca(OH)_2$ could be applied. As to the pH adjustment with acids, alternative to $HNO_3$, the options are HCl and $H_3PO_4$.

It may be advantageous to combine those chemical treatments with efforts to enrich the sugar juice and/or pulp. In this context a treatment with KOH and/or $Ca(OH)_2$ and/or $H_3PO_4$ may enrich the mash with K, Ca or P successively, whereas a treatment with $NH_4OH$ and/or $HNO_3$ may enrich the mash with N (precursor of protein). See also table 4.

New is:

The problem: The adaptation of biomass to long-term storage, handling and use as a feedstock in livestock feeding and biogas plants as well as substrate for the production of semi-manufactured products, such as sugar juice, has been hampered by a high viscosity and low control on the fermentation process under anaerobic conditions. Those two factors combined have posed a major impediment on the perspectives of biomass as a source of a homogeneous feed and of semi-manufactured products.

This invention targets two fields with the adaptation of biomass mash to long-term storage, handling and use as the common denominator. The use of the invention can be limited to the production of a feedstock in the feeding of livestock and/or biogas plants. The scope of use can be widened to the production of both sugar juice, for the production of semi-manufactured products and of pulp for the feeding of livestock and/or biogas plants.

New, compared to present-day status quo, is the destruction of pectin and of microbial life, fungi included, through an alkaline treatment subsequently combined with an acid adjustment of the pH upon choice to levels optimal for the different process-lines pursued.

Whereas the destruction of pectin leads to improved fluidity, the destruction of microbial life prevents fermentation of the biomass mash.

New, compared to the destruction of pectin by enzymes or silage additives including enzymes, is the controlled bactericidal and fungicidal effect of the invention which prevents fermentation, improves aerobic stability and allows an adjustment of the pH of the mash to optimum levels, as illustrated in table 8.

In an embodiment of the present invention the biomass may comprise pectin in an amount of 2-3% of the dry matter content.

In a further embodiment of the present invention the biomass mash may comprise pectin in an amount of less than 0.25% of the dry matter content, such as less than 0.2%, e.g. less than 0.15%, such as less than 0.1%, e.g. less than 0.05% of the dry matter content.

Compared to methods with the destruction of the lignocellulosic complex as target, among which US patent—2008 102502, the present invention addresses long-term storage and handling of biomass with less than 10% lignin, instead of 10% or more, of the dry matter in order to sustain a high feeding quality (energy-density) of the mash.

Moreover, this invention pursues low-input process conditions from 1-40° C. instead of steam at 100 degrees or more, a significantly less-harsh and better controlled alkaline treatment ranging from 9 minutes (0.15 hours) to more, instead of a duration of 2 hours or more, followed by an acid treatment to controlled pH levels upon choice in order to sustain sugar yields and sugar quality.

The add-on effects of this new combined treatment, are an improved homogenization and draining potential of the biomass mash. If the improvement of digestibility of the feedstock for feeding livestock and biogas plants is of prime concern, an alkaline treatment of longer duration can be pursued. Dependent on the bases and acids used in the treatment, the biomass mash can be enriched by Potassium (K), Calcium (Ca), Phosphor (P) and/or Nitrogen (N).

It should be noted that embodiments and features described in the context of one of the aspects of the present invention also apply to the other aspects of the invention.

All patent and non-patent references cited in the present application, are hereby incorporated by reference in their entirety.

Tables

TABLE 1

| Sources of Biomass | % OF THE DRY MATTER | |
|---|---|---|
| | Lignin | NDF |
| Alfalfa silage | 8 | 44 |
| Green alfalfa, flower bud stadium | 9 | 42 |
| Green alfalfa, 12 days after bud stadium | 9.7 | 45 |
| Corn silage, well-eared | 4 | 46 |
| Green alfalfa, poor-eared | 5 | 53 |
| Cool Season Grass silage, high quality | 2 | 50 |
| Cool Season Grass silage, typical values | 2-6 | 50-65 |
| Tropical grasses | 7-8 | |
| Grass-clover silage of good quality | 4 | 50 |
| White clover | 5 | 30 |
| Feed beets, dry matter of 22% | 2 | 11.5 |
| Feed beets + leaves | 3 | 19 |

Table 1 shows different types of plant materials which may be used as biomasses according to the present invention.

In this invention the feeding quality of biomass is of prime importance. Top quality is reflected in a low lignin and NDF content. Beets respectively the beet crop are the top performers not only in yield but also in quality per hectare, as illustrated in table 1.

In the context of the invention, biomass is defined for the organic materials with a lignin content of less than 10% and a NDF (Neutral Detergent Fiber) of less than 65% of the dry matter. Both are important criteria for estimating feeding value of forage in feeding cows and pigs, whereby the lower the value, the better the quality, whereas silage values as high or higher than 10% lignin and 65% NDF, as measured by the method P. J. van Soest (1) are too high for high performing cattle, pigs and biogas plants.

TABLE 2

| Substrate | Cp-value | ° C. |
|---|---|---|
| Water | 0 | 18 |
| Milk | 2 | 18 |
| Glucose | 4.300-8.600 | 27 |
| Malt extract-80% | 9.500 | 18 |
| Mashed potatoes | 20.000 | 38 |
| Molasses-rest product of sugar beet | 1.400-13.000 | 38 |
| Beet silage-not treated | 15-30 | 20 |
| Beet silage-treated by the method of the present invention | 2-5 | 20 |

Table 2 shows the viscosity of different fluids

Higher viscosity fluids (3) are less fluid and require a greater force to flow than do lower viscosity fluids. This is measured in Centipoise, in short Cp. Biomass is in general at the higher end of the scale. The invention destroys the pectin, improving the fluidity of e.g. beet mash by up to 70% or more on the Cp-scale.

The invention deals with the viscosity or fluidity of biomass. The high viscosity of traditional biomass mash leads to difficulties in achieving a homogeneous feedstock from day to day, which is essential in feeding high performing animals, as well as in maximizing the draining of the biomass into a liquid fraction.

TABLE 3

| Analysis of Beet Silage, in g/kg | Untreated over a number of silos | | Anticipated values by the invention |
|---|---|---|---|
| | Average value | Window of variation | |
| Sugar | 59 g/kg | 2-147 g/kg | 150 g/kg |
| pH-value | 4 | 3.5-4.5 | 1-7 upon choice |
| Lactic acid | 12 g/kg | 6-29 g/kg | 0 |
| Acetic acid | 8 g/kg | 2-18 g/kg | 0 |
| Ethanol | 37 g/kg | 4-77 g/kg | 0 |

Table 3 shows an analysis of beet silage.

Under anaerobic conditions, fermentation of sugars takes place into organic acids and alcohol, leading to pH changes. This process is difficult to control, leading to large variations from silo to silo.

The invention deals with storage and handling of biomass under anaerobic conditions. The present invention kills microbial life, such that no fermentation takes place and that the dry matter losses associated with fermentation are next to nothing whereas the final pH-value is under control.

TABLE 4

| Treatment | Added valuable mineral to the mash |
|---|---|
| Potassium hydroxide (KOH) and Calcium hydroxide (Ca(OH)$_2$) | Potassium respectively calcium |

TABLE 4-continued

| Treatment | Added valuable mineral to the mash |
|---|---|
| Ammonium hydroxide ($NH_4OH$), Urea ($CO(NH_2)_2$.) and Nitric acid ($HNO_3$,) | Nitrogen, precursor of protein |
| Phosphoric acid ($H_3PO_4$.) | Phosphor |

Table 4 shows how to enrich the biomass mash with minerals depending on the base and/or acid added to the method of the present invention.

Selecting the right base and/or acid for the treatment can enrich the mash upon choice.

The invention deals with a feedstock to animals and biogas plants. The chemical treatment can be chosen such that the biomass is enriched by valuable minerals, among others, Potassium, Calcium, Phosphor and Nitrogen, which cater to and optimize the different process-lines and products pursued.

TABLE 5

| Item | Not treated (2), Average of 3 treatments | Treated (2) with silage additives, average of 3 treatments | The present invention, the figures below are anticipated and fictive. |
|---|---|---|---|
| | Red Clover-grass silage | | Beet silage |
| Dry matter g/kg | 261 | 267 | 220 |
| Dry matter loss, % | 9.6 | 6.4 | 0 |
| pH | 4.9 | 4.4 | After choice |
| Lactic acid, bactericide g/kg | 24 | 34 | 0 |
| Acetic acid, bactericide g/kg | 25 | 39 | 0 |
| Microbial life-yeasts in log cfu/gram | 3.2 | 1.3 | 0 |
| Microbial life-moulds in log cfu/gram | 3.0 | 1.3 | 0 |
| Aerobic stability in days | 5.5 | 13 | 30 or more |

Table 5 shows the composition of Red Clover-grass silage versus beet silage of the present invention.

Aerobic stability is expressed as the number of hours/days the silage remains stable upon exposing it to the air and before temperature rises with more than 3° C. Aerobic stability leads to on-farm flexibility in time in handling biomass and is directly correlated to the death of microbial life.

In practice, silage additives are applied at a regular basis to increase aerobic stability (2). Upon treatment with additives, yeasts and molds are reduced but remain, leading to a rapid build-up of microbial life when exposed to air and a limited window of 13 days before the onset of rot. By applying the method of the present invention which kills microbial life the farmer does not need to apply expensive additives to sustain a stable biomass mash and on top of that improves the aerobic stability compared to additives by 18 days or more.

TABLE 6

| Food item in g/100 g | Total sugars | Free fructose | Free glucose | Sucrose | Sucrose as % of total sugars |
|---|---|---|---|---|---|
| Apple | 10.4 | 5.9 | 2.4 | 2.1 | 19.9 |
| Carrot | 4.7 | 0.6 | 0.6 | 3.6 | 77 |
| Sweet corn | 6.2 | 1.9 | 3.4 | 0.9 | 15 |
| Sugar cane | 13-18 | 0.2-1 | 0.2-1 | 11-16 | 84-89 |
| Sugar beet | 17-18 | 0.1-0.5 | 0.1-0.5 | 16-17 | 93-95 |

Table 6 shows the content of sugar species in crop derived biomasses.

The beet crop has a superb sucrose content compared to other biomass. Please recognize that with a dry matter content of 22% in beet, 75-80% thereof is sucrose.

The invention deals with a liquid feedstock, sugar juice, as a substrate for the production of high value products, such as crystal sugar, lactic acid for the production of bio-plastic and other bio-products. Whereas the production of crystal sugar requires sucrose, other process lines favor fructose and/or glucose. The beet crop has a superb sucrose content compared to other biomass. With beet as the favorite substrate and through control of the pH-level upon the acid treatment, this invention can provide a feedstock of a sugar quality of choice.

TABLE 7

| End product | Preferred fermentable sugar substrate | Microorganism involved in the fermentation | Optimum process pH | Process-optimization by adding |
|---|---|---|---|---|
| Crystal sugar | Sucrose | None | pH 6 | |
| Ethanol | Sucrose, glucose and fructose | Yeast *S.cerevsae* | pH 4-5 | N |
| | Sucrose, glucose and fructose | Bacterium *Z.mobilis* | pH 5-6 | N |
| Lactic acid | Glucose, lactose | *Lactobacillus delbrueckii* | Above 5.3 | N |
| Bacitracin | Glucose | *Bacillus lecheniformis* | pH 8 | N |
| Bacitracin | Glucose | *Bacillus subtilis* | pH 8 | N |

Table 7 shows how pH of the biomass mash upon the $2^{nd}$ pH adjustment influences the sugar species present in the biomass mash.

TABLE 8

The ligno-cellulosic complex of biomass on speed of digestion:

| NDS** | Rank | ADS** | Rank | ADF** | Rank |
|---|---|---|---|---|---|
| Sugar | 1 | Hemi-cellulose | 5 | Ligno-cellulose | 7 |
| Starch | 2 | Cellulose | 6 | Lignin | 8 |
| Protein | 3 | | | | |
| Pectin | 4 | | | | |
| Digested within 10 days | | Delays digestion to 28 days | | Delays digestion to 100 days | |

**Parameters of feed quality

Table 8 shows the vast differences between speed of digestion of different biomass. The slower the speed of digestion, the less the performance of livestock and biogas digesters. Sugar is digested within 2 days, whereas it takes 100 days for biogas digesters to digest lignin. It is therefore that this invention limits biomass to a lignin content of less than 10%.

The combined alkaline-acid treatment of this invention has a multifold of positive effects on biomass, which are illustrated in Table 9.

TABLE 9

Effect of the combined alkaline-acid treatment on biomass.

| Effect of patent claim | | Strong base | Additional effect of Strong acid | |
|---|---|---|---|---|
| | On biomass | Break-down of pectin | Break-down of lingo-cellulose | Bacterial and fungal death |
| Viscosity | Facilitates handling of biomass | Reduced | | |
| Water retention | | Reduced | | |
| Fixation ethanol | Improves sugar and ethanol yields (pectin binds ethanol) | Reduced | | |
| Anaerobic fermentation | | Reduced | Reduced | Reduced |
| Amount of single sugars | | Increased | Increased | |
| Digestibility | Improves handling of feed and feed value | Increased | Increased | |
| Aerobic stability | | Increased | Increased | Increased |
| Control of pH | | Total | Total | Total |

EXAMPLES

Example 1

Detailed Description of the Chemical Treatment in the Invention

Both beet or alternatively the beet crop is mashed and pulverized to a mash and subsequently mixed. NaOH respectively KOH is added to this mash to reach a pH anywhere between pH 7.5-14. After 0.15 hours or more $HNO_3$ is added to reach a pH of choice, upon which the substrate is pumped into a lagoon for storage and subsequent use, as illustrated in FIG. 1.

In more detail, the following example, from numerous possibilities, can serve. On 1 kg of the mashed beet or beet crop, a 0.4 kg NaOH solution can be added to arrive at a pH of 7 or more. After 0.15 hours or more at this pH, a 0.4 kg $HNO_3$ solution is added to arrive at a pH of choice.

Example 2

Two Scenarios to Apply the Invention in Practice at Daily Temperatures:

The invention centers on the use of the beet crop even though other biomasses may be used. The beet crop may be chosen as it provides the highest yields in dry matter and sucrose yield per hectare, by a top rank in environmental sustainability, in the cool summers of the colder climates and in the cool winters of the warmer climates.

On top of that, the beet crop, at 3% lignin and 9.5% of cellulose of the dry matter, is low in ligno-cellulose, which is of critical importance in feeding high performing livestock and biogas plants and a prerequisite for a low-input bio-energy system for whatever purpose as table 8 suggests.

So irrespective of the invention is limited to the production of a feedstock for feeding livestock or biogas plants or to produce sugar juice and pulp, the beet crop may be used.

As illustrated in FIG. 1, the harvest of the beet crop leads to two products, beets and beet tops. The beets have to be cleaned and are fed into a stationary cleaning unit (mobile unit), where the beets are washed and destoned. Subsequently they are mashed into a mash. In adding the chopped leaves a mash of the beet crop is realized and ensiled in a lagoon.

This mash is of relative high viscosity and difficult to homogenize. In order to reduce the viscosity and to ease the homogenization as well as maximize the separation of the liquid (sugar juice) and pulp fraction, the mash is sprayed with a strong base and stored for 0.15 hours or more in a container at a pH in between 7.5 or more. In this procedure, pectin is targeted and destroyed as documented in table FIG. 2.

This alkaline treatment, however has the additional advantage of destroying microorganism, fungi included. This in turn prevents the fermentation of sugars and the therewith connected dry matter losses and improvement in aerobic stability of the mash, as documented in tables 3 and 5 successively.

Subsequently, this mash of significantly reduced viscosity and microbial life at elevated pH is pumped into a lagoon, tower silo or liquid manure container for short or long term storage, where, through an acid adjustment, a pH of choice is sustained. This mash is ready for long term storage and can be pumped into a separator, which separates the sugar juice from the pulp, at whatever point of time, as illustrated in FIG. 1.

On pig- and dairy farms this will be done daily, such that the pulp can be fed on a daily basis, whereas the sugar juice can be accumulated in tanks or tower silos for prolonged periods of time. On arable farms, other time intervals might be pursued.

Another scenario could be based on a batch system in which the chemical treatment is applied on a daily basis or at regular time intervals. In this scenario, fresh beets, stored in clamps, can be the daily source, with an anaerobic storage limited to sugar juice.

REFERENCES

1. P. J. van Soest, 1963, Use of detergents in the analysis of fibrous feeds, J. Assoc. Off. Anal. Chemistry 46: 825-829.
2. J. Jatkauskas et al, 2013, Agricultural and Food Science 22: 137-144
3. Eko Hidayanto et al, 2010, Measurement of Viscosity and Sucrose concentration in aqueous solution using portable Brix meter, Berkala Fisika, Vol. 13, No 2.
4. S. Okimasu, 2014, A New Method for the Quantitative Determination of Pectin in Plant Materials by Colloid Titration, Bulletin of the Agricultural Chemical Society of Japan, Published online on 29 Jul. 2014.

Items

PATENT CLAIM: is the combined treatment of lignincellulosic biomass with NaOH to a pH of 8 or more of a duration of 0.15 hours to an unlimited number of days, at moderate temperatures of 10-30° C., followed by a treatment with $HNO_3$ to a pH anywhere in between 2-6, explicitly pursued to arrive at feed stocks of either improved viscosity, drainage, homogenization potential, better digestibility/unit time, higher sugar production levels, higher ethanol production levels, controlled pH-value, reduced storage losses, improved aerobic stability or combinations thereof in order to optimize process-lines in bio-energy, animal feed and industrial production of Bioproducts.

The invention claimed is:

1. An anaerobically stored wet biomass mash obtained by a method comprising:
providing a composition comprising a biomass, wherein the biomass comprises a Neutral Detergent Fiber (NDF) value of less than 45% of dry matter content and lignin in an amount of less than 10% of the dry matter content, and wherein the biomass is selected from the group consisting of alfalfa, corn, grass, clover, beet crop, sugar cane, pea, bean, whole crop cereal, sorghum, sunflower, and mixtures thereof;
subjecting the composition to a pH adjusting step under anaerobic conditions, in which the pH is adjusted with a base to a pH of 7.5 or more at a temperature of 1 to 40° C. for a period of at least 2 days, thereby generating a pH adjusted wet biomass mash for anaerobic storage.

2. The anaerobically stored wet biomass mash of claim 1, wherein the method further comprises subjecting the pH adjusted biomass mash to a second pH adjusting step, wherein the pH is adjusted with an acid to a pH in the range of 1-6.5.

3. The anaerobically stored wet biomass mash of claim 1, wherein the biomass is beet crop.

4. The anaerobically stored wet biomass mash of claim 3, wherein the biomass mash has a viscosity in the range from 2 to 5 Centipoise and a lignin content of 3% or lower.

5. The anaerobically stored wet biomass mash of claim 1, wherein the biomass mash comprises pectin in an amount of less than 0.1% of the dry matter content.

6. The anaerobically stored wet biomass mash of claim 1, wherein the biomass mash comprises lignin in an amount of less than 5% of the dry matter content.

7. The anaerobically stored wet biomass mash of claim 1, comprising a log Colony Forming Unit (CFU) of 0 CFUs per gram biomass mash.

8. The anaerobically stored wet biomass mash of claim 1, wherein the pH is adjusted with a base to a pH of 10 or more.

9. The anaerobically stored wet biomass mash of claim 1, wherein the temperature is in the range of 5 to 25° C.

10. The anaerobically stored wet biomass mash of claim 2, wherein the second pH adjusting step is conducted at a temperature is in the range of 5 to 25° C.

11. A method of preparing a wet biomass mash for anaerobic storage from a biomass, wherein the biomass comprises a Neutral Detergent Fiber (NDF) value of less than 45% of dry matter content and lignin in an amount of less than 10% of the dry matter content, and wherein the biomass is selected from the group consisting of alfalfa, corn, grass, clover, beet crop, pea, bean, whole crop cereal, sweet sorghum, sorghum, sun flower, and mixtures thereof, the method comprising:
providing a composition comprising the biomass; and
subjecting the composition to a first pH adjusting step, in which the pH is adjusted with a base to a pH of 7.5 or more at a temperature of 1 to 40° C. for a period of at least 2 days, thereby generating a pH adjusted wet biomass mash for anaerobic storage.

12. The method of claim 11, further comprising subjecting the pH adjusted biomass mash to a second pH adjusting step, wherein the pH is adjusted with an acid to a pH in the range of 1-6.5.

13. The method of claim 11, wherein the pH is adjusted with a base to a pH of 10 or more.

14. The method of claim 11, wherein the temperature is in the range of 5 to 25° C.

15. The method of claim 12, wherein the second pH adjusting step is conducted at a temperature in the range of 5 to 25° C.

16. The method of claim 11, wherein the biomass is beet crop.

17. The method of claim 11, wherein the base is selected from the group consisting of sodium hydroxide (NaOH), potassium hydroxide (KOH), ammonium hydroxide ($NH_4OH$), calcium hydroxide ($Ca(OH)_2$), urea ($CO(NH_2)_2$, and mixtures thereof.

18. The method of claim 12, wherein the acid is selected from the group consisting of nitric acid ($HNO_3$), phosphoric acid ($H_3PO_4$), hydrochloric acid (HCl), and mixtures thereof.

19. The method of claim 12, further comprising a step of separating the biomass mash into (i) a liquid fraction and (ii) a non-liquid fraction following the second pH adjusting step.

20. The method of claim 12, wherein before the first pH adjusting step, after the first pH adjusting step, or after the second pH adjusting step, the biomass mash is pumped into a lagoon for 1 day to a year under anaerobic conditions.

21. An anaerobic wet biomass mash, comprising:
a mash of a biomass selected from the group consisting of alfalfa, corn, grass, clover, sugar cane, beet crop, pea, bean, whole crop cereal, sweet sorghum, sorghum, sun flower, and mixtures thereof, wherein the mash comprises:
sucrose, glucose, and/or fructose;
amino acids and proteins;
lignin in an amount of less than 10% of the dry matter content;
pectin in an amount of less than 0.25% of the dry matter content;
essentially no ethanol;
essentially no lactic acid;
essentially no acetic acid;
essentially no microbial life; and
essentially no microbial colonization (CFU) activity.

22. The anaerobically stored wet biomass mash of claim 1, wherein the pH is adjusted with a base to a pH in the range from 7.5 to 14.

23. The anaerobically stored wet biomass mash of claim 1, wherein the pH is adjusted with a base to a pH in the range from 8 to 13.

24. The anaerobically stored wet biomass mash of claim 2, wherein in the second pH adjusting step, the pH is adjusted with an acid to a pH in the range of 2-5.

25. The anaerobically stored wet biomass mash of claim 2, wherein in the second pH adjusting step, the pH is adjusted with an acid to a pH in the range of 3-6.

26. The method of claim 11, wherein the pH is adjusted with a base to a pH in the range from 7.5 to 14.

27. The method of claim 11, wherein the pH is adjusted with a base to a pH in the range from 8 to 13.

28. The method of claim 12, wherein in the second pH adjusting step, the pH is adjusted with an acid to a pH in the range of 2-5.

29. The method of claim 12, wherein in the second pH adjusting step, the pH is adjusted with an acid to a pH in the range of 3-6.

\* \* \* \* \*